United States Patent
Meijer et al.

(10) Patent No.: US 11,846,886 B2
(45) Date of Patent: Dec. 19, 2023

(54) PHOTOACID GENERATOR

(71) Applicant: International Business Machines Corporation, Armonk, NY (US)

(72) Inventors: Gerhard Ingmar Meijer, Zurich (CH); Valery Weber, Zurich (CH); Peter Willem Jan Staar, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 225 days.

(21) Appl. No.: 17/101,148

(22) Filed: Nov. 23, 2020

(65) Prior Publication Data

US 2022/0163886 A1    May 26, 2022

(51) Int. Cl.
| G03F 7/26 | (2006.01) |
|---|---|
| G03F 7/004 | (2006.01) |
| C07F 7/22 | (2006.01) |
| C07F 9/92 | (2006.01) |
| C07F 9/94 | (2006.01) |

(Continued)

(52) U.S. Cl.
CPC .............. *G03F 7/26* (2013.01); *C07C 309/06* (2013.01); *C07C 309/19* (2013.01); *C07C 309/30* (2013.01); *C07C 309/39* (2013.01); *C07C 311/48* (2013.01); *C07D 285/16* (2013.01); *C07F 7/2208* (2013.01); *C07F 9/92* (2013.01); *C07F 9/94* (2013.01); *G03F 7/0045* (2013.01); *C07C 381/12* (2013.01); *C07C 2602/42* (2017.05); *G03F 7/2004* (2013.01)

(58) Field of Classification Search
CPC ......... G03F 7/2004; G03F 7/40; G03F 7/2002
See application file for complete search history.

(56) References Cited

U.S. PATENT DOCUMENTS

| 4,774,353 A | 9/1988 | Hall |
|---|---|---|
| 9,340,877 B2 * | 5/2016 | Godet ..................... G03F 7/405 |

(Continued)

FOREIGN PATENT DOCUMENTS

| CN | 114524840 A | 5/2022 |
|---|---|---|
| GB | 2603581 A | 8/2022 |

OTHER PUBLICATIONS

Barton et al., "Structural studies of crystalline pentavalent organobismuth compounds," Helvetica Chimica Acta, vol. 67(2), 1984, pp. 586-599. (Abstract).

(Continued)

*Primary Examiner* — Amanda C. Walke
(74) *Attorney, Agent, or Firm* — Brian M. Restauro

(57) ABSTRACT

The present invention relates to a novel photoacid generator compound cation, comprising an element having for 92 eV photons (extreme ultraviolet (EUV)) an absorption cross section of at least $0.5 \times 10^7 \cdot cm^2/mol$; having at least two stable oxidation states; and selected from the elements of group 1 to group 15 of the periodic table of the elements. Additionally, the present invention relates to a photoacid generator comprising said photoacid generator compound cation and an anion. Furthermore, the present invention aims to provide a photoresist composition comprising said photoacid generator and an acid labile polymer. Finally, the present invention relates to a method of generating an acid using the photoresist composition and a method of forming a patterned materials feature on a substrate.

4 Claims, 7 Drawing Sheets

(51) Int. Cl.
    *C07C 309/19*     (2006.01)
    *C07C 309/30*     (2006.01)
    *C07D 285/16*     (2006.01)
    *C07C 311/48*     (2006.01)
    *C07C 309/39*     (2006.01)
    *C07C 309/06*     (2006.01)
    *C07C 381/12*     (2006.01)
    *G03F 7/20*     (2006.01)

(56) References Cited

U.S. PATENT DOCUMENTS

| | | |
|---|---|---|
| 10,059,662 B2 | 8/2018 | Shiota |
| 10,642,153 B2 | 5/2020 | Meyers |
| 2017/0242344 A1* | 8/2017 | Carcasi .............. G03F 7/70616 |
| 2018/0039182 A1* | 2/2018 | Zi .............................. G03F 7/38 |
| 2019/0115549 A1 | 4/2019 | Snaith |
| 2019/0164745 A1* | 5/2019 | Yang ..................... H01L 21/266 |
| 2019/0310552 A1 | 10/2019 | Asano |
| 2019/0391481 A1* | 12/2019 | Xu ......................... G03F 7/2004 |
| 2020/0041901 A1 | 2/2020 | Namgung |
| 2020/0103754 A1 | 4/2020 | Bristol |
| 2020/0165730 A1 | 5/2020 | Warner |
| 2020/0272050 A1 | 8/2020 | Robinson |

OTHER PUBLICATIONS

Combined Search and Examination Report, Application No. GB2116056.9, dated May 20, 2022, 8 pages.

Fujiwara et al., "Tetraphenylstibonium triflate as a regio- and chemoselective catalyst in the reaction of oxiranes with amines," Tetrahedron Letters vol. 30(6), 1989, pp. 739-742. (Abstract).

Passarelli et al., "Bismuth Resists for EUV Lithography," Journal of Photopolymer Science and Technology vol. 27 (5), 2014, pp. 655-661.

Ruether et al., "Synthesis of tetraphenylstibonium alkane and arene sulfonates. Crystal structure of tetraphenylstibonium benzenesulfonate hydrate," Journal of Organometallic Chemistry vol. 295(1), 1985, pp. 21-28. (Abstract).

Sharutin et al., "Synthesis and structure of tetra- and triphenylbismuth arenesulfonates," Russian Chemical Bulletin (Translation of Izvestiya Akademii Nauk, Seriya Khimicheskaya) vol. 48(12), 1999, pp. 2325-2329. (Abstract).

Sharutin et al., "Tetra- and triphenylantimony sulfonates," Russian Journal of General Chemistry (Translation of Zhurnal Obschchei Khimii) vol. 67(9), 1997, pp. 1438-1442. (Abstract).

\* cited by examiner

PHOTOACID GENERATOR

BACKGROUND

The present invention relates to the field of photoacid generators (PAGs). More specifically, the present invention relates to a new photoacid generator for chemically amplified photoresists for EUV lithography.

Photoresists are photosensitive films for transfer of patterns to a substrate. They form negative or positive patterns. After coating a photoresist on a substrate, a source of activating energy, such as ultraviolet light, is used to project a patterned mask or reticle, typically using a so-called stepper and a 4× reduction lens assembly, onto the coating to form a latent pattern in the photoresist coating. The mask defines the pattern desired to be transferred to the underlying substrate.

Chemical amplification-type photoresists have proven to be useful in achieving high sensitivity in processes for forming patterns with small feature sizes in semiconductor manufacturing. These photoresists are prepared by blending a photoacid generator with a polymer matrix having acid labile structures. According to the reaction mechanism of such a photoresist, the photoacid generator generates acid when it is irradiated by the light source, and the main chain or branched chain of the polymer matrix in the exposed or irradiate portion reacts with the generated acid and is decomposed or cross-linked, so that the polarity of the polymer is altered. This alteration of polarity results in a solubility difference in the developing solution between the irradiated exposed area and the unexposed area, thereby forming a positive or negative pattern of a mask on the substrate.

Extreme ultraviolet (EUV) lithography is being used as one essential technology for semiconductor manufacturing of next generation devices. EUV lithography is a technology platform that uses an EUV ray having a wavelength of about 13.5 nm, which corresponds to an energy of about 92 eV, as an exposure light source. With the help of the EUV lithography, patterns with very small feature sizes (e.g., patterns having a width or critical dimension of less than or equal to about 20 nm) may be formed in an exposure process during a manufacturing of a semiconductor device.

Currently, photoresists for EUV lithography of the 7-nm and 5-nm technology nodes are polymer-based chemically amplified photoresists. These photoresist platforms comprise the following components:
(1) Photoacid generator: The PAG decomposes upon ultraviolet (UV) exposure; an acid is generated along with degradation products. Commonly used PAGs are based on sulfonium salts, for example, triphenylsulfonium triflate. Upon UV exposure, the sulphur-carbon (S—C) bond in the sulfonium salts undergoes radical cleavage and an acid is generated.
(2) Acid-labile polymer: The acid-labile protection group of this polymer can be removed by an acid. The thereby generated compounds are alkali-soluble or volatile.

A key metric of the photoresist is its sensitivity. Sensitivity is the UV dose that is required to print a feature in the photoresist. Currently available chemically amplified photoresists for EUV lithography have generally a too low sensitivity. The material's toxicity and chemical waste are in focus too. Currently available chemically amplified photoresists for EUV lithography have generally a material's toxicity and chemical waste pain-point.

Inorganic photoresists based on metal oxides have been disclosed. This photoresist platform comprises organotin clusters. Upon EUV exposure the Sn—C bonds dissociate and the inorganic SnOx clusters crosslink. This leads to a change of solubility. The not exposed material is soluble in alkaline solvents whereas the exposed material is not. While inorganic photoresists for EUV lithography have generally a high sensitivity, mitigating process-integration risks is challenging: the industry is reluctant to change the chemically amplified photoresists platforms.

In some instances, incorporation of In, Sn, Sb, Te, Tl, Pb, Bi, and Po in an organometallic compound is possible. Said "passive" organometallic component can be admixed to chemically amplified photoresists for EUV lithography to increase the sensitivity in the EUV. The increase of sensitivity in the EUV is however modest, because said "passive" organometallic component is not part of the chemically amplified photoresists' PAG, which actively participates in the EUV-photon induced chemical reactions.

In other instances, a radiation-sensitive composition can be used in EUV lithography, and includes a first polymer and a solvent. The first polymer includes a first structural unit including: at least one metal atom; and at least one carbon atom that each bonds to the metal atom by a chemical bond. The metal atom is preferably Ge, Sn, and Pb, which is incorporated in the acid-labile polymer of the photoresist. The increase of sensitivity in the EUV is however modest, because said "passive" organometallic component is not part of the chemically amplified photoresists' PAG, which actively participates in the EUV-photon induced chemical reactions.

Other photoresists for EUV lithography include a polymer with one repeating unit and an absorbing unit. In the acid-labile polymer Bi, Co, Fe, Ge, and P are incorporated. The increase of sensitivity in the EUV is however modest, because said "passive" organometallic component is not part of the chemically amplified photoresists' PAG, which actively participates in the EUV-photon induced chemical reactions.

The foregoing indicates a need for chemically amplified photoresists for EUV lithography having a high sensitivity and posing a limited process-integration risk. Additionally, there is a need for chemically amplified photoresists which have a low material's toxicity and chemical waste.

SUMMARY

To achieve these and other advantages, and in accordance with the purpose of the present invention as embodied and broadly described herein, the invention comprises a novel photoacid generator, in particular a photoacid generator compound cation, comprising an element that (i) has a high absorption cross section for photons in the EUV; (ii) has at least two stable oxidations states; and (iii) is selected from the elements of group 1 to group 15 of the periodic table of elements, preferably the elements indium (In), tin (Sn), antimony (Sb), thallium (Tl), lead (Pb), or bismuth (Bi). The photoacid generator's compound cation molecular structure is chosen such that upon EUV exposure and In—C, Sn—C, Sb—C, Tl—C, Pb—C, or Bi—C bond radical cleavage, the generated intermediate radicals $R_{n-1}In^+\blacksquare$, $R_{n-1}Sn^+\blacksquare$, $R_{n-1}Sb^+\blacksquare$, $R_{n-1}Tl^+\blacksquare$, $R_{n-1}Pb^+\blacksquare$, or $R_{n-1}Bi^+\blacksquare$, where "$\blacksquare$" indicates a radical and n=2 for the In and Tl compounds, n=3 for the Sn and Pb compounds, and n=4 for the Sb and Bi compounds, are stabilized by groups R. When the reaction is completed, a proton $H^+$ is released along with degradation products, in which In, Sn, Sb, Tl, Pb, or Bi are in a reduced oxidation state. The proton $H^+$ combines with the photoacid generator's anion to form the Brønsted acid (or, in some cases, a Lewis acid) that further participates in the photolithography process. The present invention comprises the formulation and use of photoresists employing these PAGs that are optimized for absorption characteristics required for EUV photons. Incorporation of these PAGs can increase the sensitivity or photospeed of chemical amplified photoresists for EUV lithography.

In a first aspect, the present invention relates to a photoacid generator compound cation of the general formula (I)

$$R_n\text{-}X^+ \quad (I)$$

wherein

X represents an element
(i) having for 92 eV photons (extreme ultraviolet (EUV)) an absorption cross section of at least $0.5 \times 10^7 \cdot cm^2/mol$;
(ii) having at least two stable oxidation states; and
(iii) selected from the elements of group 1 to group 15 of the periodic table of the elements; R represents a linear or branched or a cyclic unsubstituted or substituted alkyl group having 1 to 20 carbon atoms; or an unsubstituted or substituted aryl group having 3 to 30 carbon atoms;
or an unsubstituted or substituted unsaturated or saturated heterocyclic group having a 3 to 30 membered ring; or derivatives thereof;
wherein the R groups are either separated from each other or at least two R groups are linked with each other; and
n is 2 to 5.

In another aspect, the present invention relates to a photoacid generator comprising the photoacid generator compound cation according to the present invention and an anion.

In another aspect, the present invention relates to a photoresist composition comprising
(a) a photoacid generator according to the present invention; and
(b) an acid labile polymer.

In a further aspect, the present invention relates to a method for generating an acid, comprising the steps of: applying a photoresist composition according to the present invention to a substrate, the photoresist composition containing a photoacid generator according to the present invention, and irradiating the photoresist composition with an energy ray to cause the photoacid generator to generate an acid.

Finally, in a still further aspect, the present invention relates to a method of forming a patterned materials feature on a substrate, comprising the steps of: providing a material surface on a substrate; forming a layer of the photoresist composition according to the present invention over said material surface; patternwise irradiating the photoresist layer with an energy ray thereby creating a pattern of radiation-exposed regions in said photoresist layer; selectively removing portions of said photoresist layer to form exposed portions of said material surface; and etching or ion implanting said exposed portions of said material, thereby forming said patterned material feature.

The present invention provides a new photoacid generator compound cation and a photoacid generator, that have a high absorption cross section for photons in the EUV to increase the sensitivity of chemical amplified photoresists for EUV lithography.

The chemically amplified photoresists for EUV lithography that comprise the photoacid generator compound cation and the photoacid generator described herein, also pose limited process-integration risks because the process flow in the fab's photobay is unchanged. Some embodiments have a material's toxicity and chemical waste advantage.

Various variants provide a photoacid generator compound cation, a photoacid generator, a photoresist composition and methods, as described by the subject matter of the independent claims. Advantageous variants are described in the dependent claims. Embodiments of the present invention can be freely combined with each other if they are not mutually exclusive.

BRIEF DESCRIPTION OF THE DRAWINGS

Preferred embodiments of the present invention will now be described, by way of example only, with reference to the following drawings, in which.

DETAILED DESCRIPTION

Figure 1:
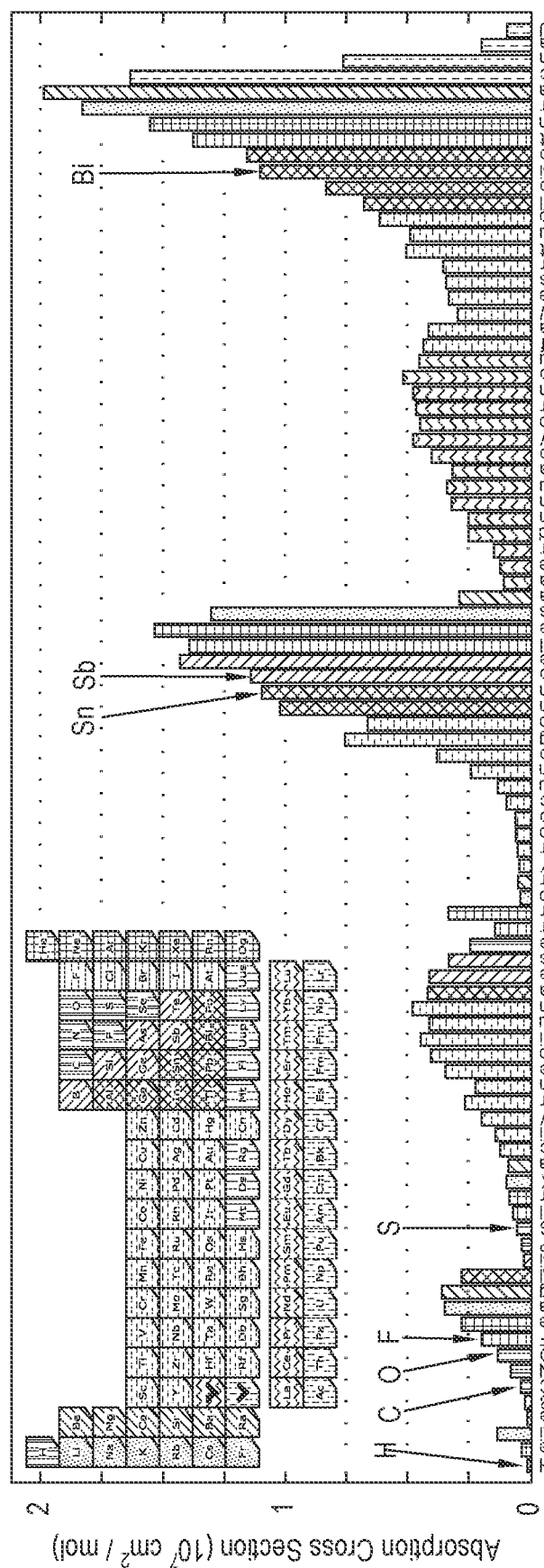
FIG. 1 displays the photo absorption cross-section $\mu_a$ at 92 eV of all naturally occurring elements.

Embodiments of the present invention recognize a need for chemically amplified photoresists for EUV lithography having a high sensitivity and posing a limited process-integration risk. Additionally, there is a need for chemically amplified photoresists which have a low material's toxicity and chemical waste. Accordingly, an object of the present invention is to provide a new photoacid generator compound cation and a photoacid generator, and a photoresist composition that comprises said new photoacid generator, that increase the sensitivity of chemically amplified photoresists for EUV lithography and which pose limited process-integration risks. The present invention further aims to provide a photoacid generator that has a material's toxicity and chemical waste advantage. In particular, embodiments of the present invention provide an improved a photoacid generator comprising a new photoacid generator compound cation, and a photoresist composition, comprising said photoacid generator compound. Finally, the present invention relates to a method of generating an acid using said photoresist composition and a method of forming a patterned materials feature on a substrate.

The descriptions of the various embodiments of the present invention will be presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Unless otherwise stated, the following terms used in this application, including the specification and claims, have the definitions given below. It must be noted that, as used in the specification and the appended claims, the singular forms "a," "an," and "the" include plural referents unless the context clearly dictates otherwise.

As used herein, the term "moiety" refers to a specific segment or functional group of a molecule. Chemical moieties are often recognized chemical entities embedded in or appended to a molecule.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing from 1 to 20 (e.g., 2 to 18, 3 to 18, 1 to 8, 1 to 6, 1 to 4, or 1 to 3) carbon atoms. An alkyl group can be straight, branched, cyclic or any combination thereof. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents or can be multicyclic as set forth below.

Unless specifically limited otherwise, the term "alkyl," as well as derivative terms such as "alkoxy" and "thioalkyl," as used herein, include within their scope, straight chain, branched chain, and cyclic moieties.

As used herein, an "alkenyl" group refers to an aliphatic carbon group that contains from 2 to 20 (e.g., 2 to 18, 2 to 8, 2 to 6, or 2 to 4) carbon atoms and at least one double bond. Like an alkyl group, an alkenyl group can be straight, branched or cyclic or any combination thereof.

Examples of an alkenyl group include, but are not limited to, allyl, isoprenyl, 2-butenyl, and 2-hexenyl. An alkenyl group can be optionally substituted with one or more substituents as set forth below.

As used herein, an "alkynyl" group refers to an aliphatic carbon group that contains from 2 to 20 (e.g., 2 to 8, 2 to 6, or 2 to 4) carbon atoms and has at least one triple bond. An alkynyl group can be straight, branched or cyclic or any combination thereof. Examples of an alkynyl group include, but are not limited to, propargyl and butynyl. An alkynyl group can be optionally substituted with one or more substituents as set forth below.

As used herein, the term "alicyclic" refers to an aliphatic ring compound or group comprising at least three carbon atoms and the bonds between pairs of adjacent atoms may all be of the type designated single bonds (involving two electrons), or some of them may be double or triple bonds (with four or six electrons, respectively).

A "halogen" is an atom of the group 17 of the periodic table of elements, which includes fluorine, chlorine, bromine, and iodine.

As used herein, an "aryl" group refers to an aromatic ring compound or group having 3 to 30 carbon atoms and used alone or as part of a larger moiety as in "aralkyl," "aralkoxy," or "aryloxyalkyl" and refers to monocyclic (e.g., phenyl); bicyclic (e.g., indenyl, naphthalenyl, tetrahydronaphthyl, or tetrahydroindenyl); and tricyclic (e.g., fluorenyl, tetrahydrofluorenyl, tetrahydroanthracenyl, or anthracenyl) ring systems in which the monocyclic ring system is aromatic or at least one of the rings in a bicyclic or tricyclic ring system is aromatic. The bicyclic and tricyclic groups include benzofused 2 to 3 membered carbocyclic rings. For example, a benzofused group includes phenyl fused with two or more $C_4$ to $C_8$ carbocyclic moieties. An aryl is optionally substituted with one or more substituents as set forth below.

As used herein, an "aralkyl" or "arylalkyl" group refers to an alkyl group (e.g., a $C_1$ to $C_4$ alkyl group) that is substituted with an aryl group. Both "alkyl" and "aryl" have been defined above. An example of an aralkyl group is benzyl. An aralkyl is optionally substituted with one or more substituents as set forth below.

As used herein, a "cycloalkyl" group refers to a saturated carbocyclic mono- to pentacyclic (fused or bridged) ring of 3 to 20 (e.g., 5 to 20) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, azacycloalkyl, or ((aminocarbonyl)cycloalkyl) cycloalkyl.

As used herein, the term "heteroaryl" group refers to a monocyclic, bicyclic, or tricyclic ring system having 3 to 30 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents as is set forth below.

A "heteroarylalkyl" group, as used herein, refers to an alkyl group (e.g., a $C_1$ to $C_4$ alkyl group) that is substituted with a heteroaryl group. Both "alkyl" and "heteroaryl" have been defined above. A heteroarylalkyl is optionally substituted with one or more substituents as is set forth below.

As used herein, an "acyl" group refers to a formyl group or $R^X$—C(O)— (such as -alkyl-C(O)—, also referred to as "alkylcarbonyl") where "alkyl" has been defined previously.

As used herein, the term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups.

As used herein, an "alkoxy" group refers to an alkyl-O— group where "alkyl" has been defined previously.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, "alkoxycarbonyl" means —COOR, where R is alkyl as defined above, e.g., methoxycarbonyl, ethoxycarbonyl, and the like.

As used herein, a "sulfinyl" group refers to —S(O)—R$^X$ when used terminally or —S(O)— when used internally.

As used herein, a "sulfonyl" group refers to —S(O)$_2$—R$^X$ when used terminally or —S(O)$_2$— when used internally.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In certain embodiments, lower alkylthios are contemplated.

As used herein, the term "amine" or "amino" includes compounds where a nitrogen atom is covalently bonded to at least one carbon or heteroatom. The term "amine" or "amino" also includes —NH$_2$ and also includes substituted moieties. The term includes "alkyl amino" which comprises groups and compounds wherein the nitrogen is bound to at least one additional alkyl group. The term includes "dialkyl amino" groups wherein the nitrogen atom is bound to at least two additional independently selected alkyl groups. The term includes "arylamino" and "diarylamino" groups wherein the nitrogen is bound to at least one or two independently selected aryl groups, respectively.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to five halogen atoms.

The phrase "optionally substituted" is used interchangeably with the phrase "substituted or unsubstituted." As described herein, compounds of the present disclosure can optionally be substituted with one or more substituents, such as are illustrated generally above, or as exemplified by particular classes, subclasses, and species of the present disclosure. As described herein any of the above moieties or those introduced below can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkyl sulfonyl and the alkyl sulfonyl can be optionally substituted with one to three of halo, cyano, oxoalkoxy, hydroxy, amino, nitro, aryl, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this present disclosure are those combinations that result in the formation of stable or chemically feasible compounds.

Modifications or derivatives of the compounds disclosed throughout this specification are contemplated as being useful with the methods and compositions of the present disclosure. Derivatives may be prepared and the properties of such derivatives may be assayed for their desired properties by any method known to those of skill in the art. In certain aspects, "derivative" refers to a chemically modified compound that still retains the desired effects of the compound prior to the chemical modification.

The photoacid generator compound cation according to the present disclosure can be used as photoacid generator as will be explained in more detail below. The term "photoacid generator" means a compound capable of producing an acid by decomposition of its chemical structure when irradiated with light.

Surprisingly, it has been discovered that the PAG compound cations of the present disclosure are characterized by excellent photo-reactivity for EUV radiation.

The present invention provides photoacid generators to be formulated into polymer compositions that are useful in lithographic processes, especially when EUV radiation is used. In carrying out the present invention, conventional materials and processing techniques can be employed and, hence, such conventional aspects are not set forth herein in detail. For example, the selection of suitable acid labile polymers, base quenchers, and solvents is conducted in a conventional manner.

In one aspect, the present invention relates to a photoacid generator compound cation of the general formula (I)

$$R_n\text{-}X^+ \tag{I}$$

wherein
X represents an element
(i) having for 92 eV photons (extreme ultraviolet (EUV)) an absorption cross section of at least $0.5 \times 10^7 \cdot cm^2/mol$;
(ii) having at least two stable oxidation states; and
(iii) selected from the elements of group 1 to group 15 of the periodic table of the elements; R represents a linear or branched or a cyclic unsubstituted or substituted alkyl group having 1 to 20 carbon atoms; or an unsubstituted or substituted aryl group having 3 to 30 carbon atoms; or an unsubstituted or substituted unsaturated or saturated heterocyclic group having a 3 to 30 membered ring; or derivatives thereof;
wherein the R groups are either separated from each other or at least two R groups are linked with each other; and n is 2 to 5.

The photoacid generator compound cation of the general formula (I) is characterized in that it comprises an element X that has for 92 eV photons an absorption cross section of at least $0.5 \times 10^7 \cdot cm^2/mol$.

FIG. 1 displays the photo absorption cross-section $\mu_a$ at 92 eV of all naturally occurring elements. The absorption of photons in a layer of thickness d is given by $1-\exp(-n \mu_a d)$, where n is the number of atoms per unit volume in the layer.

In order to devise photoacid generators that can be used to increase the sensitivity of chemically amplified photoresists for EUV lithography, it is crucial to understand and to appreciate the microscopic mechanisms that cause photon absorption events and that cause photoacid generator decomposition in the EUV, in contrast to in the DUV.

The DUV (193 nm or 248 nm, 6 eV or 5 eV, respectively) photon absorption is determined by the molecular orbitals of the photoresist material. The absorbed photons can directly and selectively cause resonant electronic transition in the photoacid generator, resulting in the generation of an acid. The sensitivity of chemically amplified photoresists for DUV lithography can be increased by adjusting the molecular structure of the photoacid generator.

By contrast, the EUV (13.5 nm, 92 eV, soft X-ray) photon absorption is determined by the atomic composition of the photoresist material, i.e., the molecular structure is essentially not relevant.

DUV photoresist platforms are mainly composed of light elements such as H, C, O, F, and S, which all have for 92 eV photons a low absorption cross section. This limits their EUV performance.

To increase the chemically amplified photoresists' 92 eV photon absorption cross section, elements that have a large absorption cross section at this photon energy must be added directly to the photoresist composition.

Embodiments of the present invention recognize, surprisingly, that in EUV lithograph the absorbed photon ionizes an atom in the photoresist. The photoelectron (about 80 eV) subsequently causes a cascade of nonradiative processes. Inelastic scattering from the valence electrons is the major loss mechanism for incident electrons at this energy range. The electron's inelastic scattering mean-free-path is in the order of 1 Å at 80 eV to 10 Å at 10 eV. The lower-energy electrons (<10 eV) cause electronic transitions in the photoacid generator, resulting in the generation of the acid.

Furthermore, it was realized that, because the electrons have a short inelastic scattering mean-free-path, it is advantageous to incorporate these elements directly in the photoacid generator to ensure that secondary electrons are present in the proximity of the photoacid generator. This is an advantage over the prior art, for example, US 20190310552 A1 or US 20200103754 A1, where the metal atom is incorporated in the acid-labile polymer of the photoresist, or US 20200041901 A1 where the metal atom is incorporated in a "passive" compound admixed to the photoresist.

In order to advantageously increase the 92 eV absorption in the chemically amplified photoresist, the element of the photoacid generator compound cation must have an absorption cross section for 92 eV photons of at least $0.5 \times 10^7 \cdot cm^2/mol$. In a preferred variant of the present invention, the element of the photoacid generator compound cation must have an absorption cross section for 92 eV photons of at least $0.75 \times 10^7 \cdot cm^2/mol$. In a particularly preferred variant of the present invention, the element of the photoacid generator compound cation must have an absorption cross section for 92 eV photons of at least $1.0 \times 10^7 \cdot cm^2/mol$.

Additionally, the element to be successfully incorporated in the photoacid generator, in particular in the photoacid generator compound cation, must have at least two stable oxidation states that are separated by two elementary charges.

In a preferred variant, the elements advantageously incorporated in the photoacid generator have the oxidations states 1+ and 3+; 2+ and 4+; 3+ and 5+; or 4+ and 6+.

As can be derived from FIG. 1, the elements having an absorption cross section for 92 eV photons of at least $0.5 \times 10^7 \cdot cm^2/mol$ are preferably selected from the group consisting of the elements In, Sn, Sb, Tl, Pb, and Bi.

In a more preferred variant of the present invention, the elements of the photoacid generator compound cation having an absorption cross section for 92 eV photons of at least $0.75\times10^7\cdot cm^2/mol$ are selected from the group consisting of In, Sn, Sb, Pb, and Bi.

In a particularly preferred variant of the present invention, the elements of the photoacid generator compound cation having an absorption cross section for 92 eV photons of at least $1.0\times10^7\cdot cm^2/mol$ are selected from the group consisting of In, Sn, Sb, and Bi.

The elements of the photoacid generator compound cation having the above specified absorption cross section for 92 eV photos result in a better sensitivity, when incorporated directly in the photoacid generator according to the present invention.

Additionally, the elements In, Sn, Sb, and Bi are particularly preferred under toxicity consideration since organometallic compounds comprising Tl and Pb are toxic.

Additionally, the elements Sn, Sb, and Bi are particularly preferred in comparison to the element In since organometallic compounds comprising In exhibit at room temperature less stable photoreactions.

By contrast, the elements Te and Po belonging to the group 16 of the periodic table of the elements, and, thus, not covered by the definition of the element X of the general formula (I) of the present invention, are excluded since organometallic compounds comprising Te and Po are prohibitively toxic.

Elements with said at least two stable oxidation states include the elements In (oxidation states include 1+ and 3+), Sn (oxidation states include 2+ and 4+), Sb (oxidation states include 3+ and 5+), Tl (oxidation states include 1+ and 3+), Pb (oxidation states include 2+ and 4+), and Bi (oxidation states include 3+ and 5+). Preferred elements include Sn (oxidation states 2+ and 4+), Sb (oxidation states 3+ and 5+), and Bi (oxidation states 3+ and 5+).

Moreover, the element X of the photoacid generator compound cation of general formula (I) according to the present invention is selected from the elements of group 1 to group 15 of the periodic table of the elements. Preferably, the element X is selected from the elements of group 13, 14, and 15 of the periodic table of the elements. The element X of the photoacid generator compound cation of the general formula (I) of the present invention is not an element of the group 16 of the periodic table of the elements, in particular is not Te or Po due to their toxicity.

Hence, in a more preferred variant the element X of the photoacid generator compound cation of the general formula (I) which fulfil the three requirements specified above, namely for 92 eV photons an absorption cross section of at least $0.5\times10^7\cdot cm^2/mol$, at least two stable oxidation states and selected from the elements of group 1 to group 15 of the periodic table of the elements is selected from the group consisting of In, Sn, Sb, Tl, Pb, and Bi. In a particular preferred variant the element X of the photoacid generator compound cation of the general formula (I) is selected from the group consisting of Sn, Sb, and Bi.

The photoacid generator compound cation of the general formula (I) further comprises at least two organic group(s) R. The number of the organic R group depends on the oxidation state of the element X in the general formula (I). R in the general formula (I) represents a linear or branched or a cyclic unsubstituted or substituted alkyl group having 1 to 20 carbon atoms; or an unsubstituted or substituted aryl group having 3 to 30 carbon atoms; or an unsubstituted or substituted unsaturated or saturated heterocyclic group having a 3 to 30 membered ring; or derivatives thereof.

With regard to the terms "unsubstituted or substituted aryl group", "unsubstituted or substituted unsaturated or saturated heterocyclic group" or "derivatives", reference is made to the above general definitions.

Especially preferred, the linear or branched alkyl group is selected from the group consisting of methyl, ethyl, butyl, pentyl, hexyl, heptyl, octyl, nonyl decyl, undecyl, dodecyl, tridecyl, tetradecyl, pentadecyl, hexadecyl, heptadecyl, octadecyl, nonadecyl, icosayl and derivatives thereof; and/or the cyclic alkyl group is selected from the group consisting of cyclopentane, cyclohexane, cycloheptane, cyclooctane and derivatives thereof; and/or the aryl group is selected from the group consisting of phenyl, naphthyl and derivatives thereof; and/or the saturated or unsaturated heterocyclic group having one or two heteroatoms is selected from the group consisting of pyrrolidine, pyrrole, tetrahydrofuran, furan, tetrahydrothiophene, thiophene, imidazolidine, imidazole, oxazolidine, oxyzole, thiazolidine, thiazole, dioxolane, dithiolane, piperidine, pyridine, tetrahydropyran, pyran, thiane, thiopyran, diazinane, diazine, in particular pyridazin (1,2-diazin), pyrimidine (1,3-diazin) and pyrazin (1,4-diazin), morpholine, oxazine, thiomorpholine, thiazine, dioxane, dioxine, dithiane, dithiin, quinolone, isoquinoline and derivatives thereof.

Modifications or derivatives of the compounds disclosed throughout this specification are contemplated as being useful with the methods and compositions of the present disclosure. Derivatives may be prepared and the properties of such derivatives may be assayed for their desired properties by any method known to those of skill in the art. In certain aspects, "derivative" refers to a chemically modified compound that still retains the desired effects of the compound prior to the chemical modification.

Due to their delocalized electrons, aryl groups or aromatic cycles and unsaturated heterocyclic groups, are more stable and, thus particularly preferred as appropriate R group(s) in the general formula (I) of the photoacid generator compound cation, compared for example to alkyl groups.

Aromatic groups such as phenyl, naphthyl, and their derivatives, and unsaturated heterocyclic groups such as pyridinyl, thiophenyl, and their derivatives are particularly preferred in the photoacid generator compound cation according to the present invention.

In a preferred variant, the one or more organic group(s) R of the general formula (I), namely the alkyl group or the aryl group or the heterocyclic group is/are optionally substituted. The phrase "optionally substituted" is used interchangeably with the phrase "substituted or unsubstituted." As described herein, compounds of the present disclosure can optionally be substituted with one or more substituents, such as are illustrated generally above, or as exemplified by particular classes, subclasses, and species of the present disclosure. As described herein any of the above moieties or those introduced below can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl.

The term "substituted," whether preceded by the term "optionally" or not, refers to the replacement of hydrogen radicals in a given structure with the radical of a specified substituent. Specific substituents are described above in the definitions and below in the description of compounds. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom.

In a preferred variant, the one or more organic group(s) R of the general formula (I), namely the alkyl group or the aryl group or the heterocyclic group, include(s) at least one substituent selected from the group consisting of halogen, hydroxyl, alkyl, alkoxy, aryl, aryloxy, nitro, and cyano.

The element X in the general formula (I) can either have two or more R groups which are identical or can have two or more R groups which are different. In a preferred variant, the element X in the photoacid generator cation has identical R groups.

The at least two R groups of the photoacid generator compound cation of the general formula (I) are either separated from each other or the at least two R groups are linked with each other. The term "separated from each other" means that the R groups are not interconnected or linked with each other. The term "at least two R groups are linked with each other" means that two or even more than two R groups are linked with each other or interconnected. In a preferred variant, the R groups of the photoacid generator compound cation of the general formula (I) are separated from each other. In a particularly preferred variant, two R groups of the photoacid generator compound cation of the general formula (I) are linked with each other.

The bond between the at least two R groups can be a covalent bond between any of two C atoms of the two R groups. Alternatively, the at least two R groups can be linked via a linking atom or linking group. The linking atom or linking group is preferably selected from the group consisting of —C—, —O—, —S—, —C(O)—, —S(O)—, and —S(O)$_2$—. In a preferred variant according to the present invention, two of the R groups of the element X of the photoacid generator cation of the general formula (I) are connected via a covalent bond between any two carbon atoms of the two R groups. If the at least two R groups are linked with each other, a multicycle ring is formed defined by the linkage of the two R groups and the linkage of the two R groups to the element X of the photoacid generator cation of the general formula (I). The number of the multicycle ring depends on the linkage site or binding site between the first and second R group. Preferably, the multicycle ring is a four-membered ring, a five-membered ring, a six-membered ring, a seven-membered ring, etc. If the at least two linked R groups are phenyl groups, the ring formed by the linkage is a five-membered ring. Preferred PAG cations according to the present invention, in which two R groups are linked with each other with a covalent bond between two C atoms of the two R groups, are depicted in FIGS. 2(d) to (f).

The "n" in the general formula (I) represents an integer from 2 to 5, depending on the oxidation state of the element X. For an element X with the following oxidation states, the following integer results:
 oxidation states 1+ and 3+: n=2;
 oxidation states 2+ and 4+: n=3;
 oxidation states 3+ and 5+: n=4; and
 oxidation states 4+ and 6+: n=5.

The photoacid generator compound cation according to the present invention is preferably selected from the group consisting of:
diphenylindium (Ph$_2$In$^+$, with In(III)),
2,2'-biphenylylene-indium (with In(III))),
triphenyltin (Ph$_3$Sn$^+$, with Sn(IV)),
2,2'-biphenylylene-phenyltin (with Sn(IV)),
tetraphenylantimony (Ph$_4$Sb$^+$, with Sb(V)),
2,2'-biphenylylene-diphenylantimony (with Sb(V)),
diphenylthallium (Ph$_2$Tl$^+$, with Tl(III)),
2,2'-biphenylylene-thallium (with Tl(III)),
triphenyllead (Ph$_3$Pb$^+$, with Pb(IV)),
2,2'-biphenylylene-phenyllead (with Pb(IV)),
tetraphenylbismuth (Ph$_4$Bi$^+$, with Bi(V)), and
2,2'-biphenylylene-diphenylbismuth (with Bi(V)).

Figure 2:
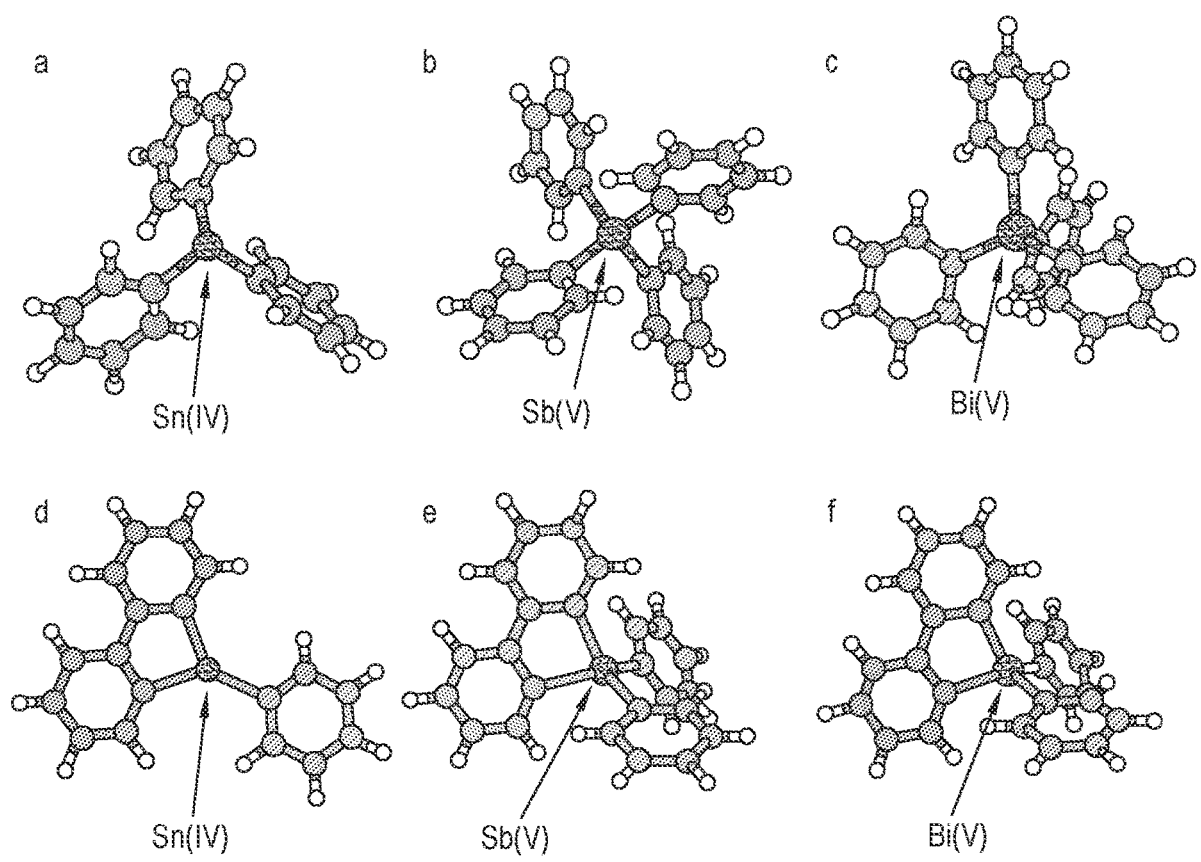
FIG. 2 displays preferred PAG cations, in accordance with an embodiment of the present invention:
(a) PAG cation triphenyltin ($Ph_3Sn^+$, with Sn(IV));
(b) PAG cation tetraphenylantimony ($Ph_4Sb^+$, with Sb(V));
(c) PAG cation tetraphenylbismuth ($Ph_4Bi^+$, with Bi(V));
(d) PAG cation 2,2'-biphenylylene-phenyltin (with Sn(IV));
(e) PAG cation 2,2'-biphenylylene-diphenylantimony (with Sb(V)); and
(f) PAG cation 2,2'-biphenylylene-diphenylbismuth (with Bi(V)).

The six specified compound cations triphenyltin, 2,2'-biphenylylene-phenyltin, tetraphenylantimony, 2,2'-biphenylylene-diphenylantimony, tetraphenylbismuth, and 2,2'-biphenylylene-diphenylbismuth are shown in FIG. 2.

In a particular preferred variant, the photoacid generator compound cation according to the present invention is selected from the group consisting of triphenyltin, 2,2'-biphenylylene-phenyltin, tetraphenylantimony, 2,2'-biphenylylene-diphenylantimony, tetraphenylbismuth, and 2,2'-biphenylylene-diphenylbismuth.

The photoacid generator compound cation's molecular structure is chosen such that upon exposure by EUV radiation one or even more In—C, Sn—C, Sb—C, Tl—C, Pb—C, or Bi—C bond is/are radically cleaved. In a preferred variant, one In—C, Sn—C, Sb—C, Tl—C, Pb—C, or Bi—C bond is radically cleaved. Upon radical cleavage of the In—C, Sn—C, Sb—C, Tl—C, Pb—C, or Bi—C bond, an intermediate radical $R_{n-1}$In$^+$■, $R_{n-1}$Sn$^+$■, $R_{n-1}$Sb$^+$■, $R_{n-1}$Tl$^+$■, $R_{n-1}$Pb$^+$■, or $R_{n-1}$Bi$^+$■, where "■" indicates a radical and n=2 for the In and Tl compounds, n=3 for the Sn and Pb compounds, and n=4 for the Sb and Bi compounds, is generated. The corresponding intermediate radicals are shown exemplary for Sn, Sb, and Bi in FIG. 3:
 (a) PAG cation triphenyltin (Ph$_3$Sn$^+$, with Sn(IV)), Sn—C radical bond cleavage and intermediate radicals (Ph■ and Ph$_2$Sn$^+$■);
 (b) PAG cation tetraphenylantimony (Ph$_4$Sb$^+$, with Sb(V)), Sn—C radical bond cleavage and intermediate radicals (Ph■ and Ph$_3$Sb$^+$■); and
 (c) PAG cation tetraphenylbismuth (Ph$_4$Bi$^+$, with Bi(V)), Bi—C radical bond cleavage and intermediate radicals (Ph■ and Ph$_3$Bi$^+$■).

Next, the intermediate radical, such as $R_{n-1}$In$^+$■, $R_{n-1}$Sn$^+$■, $R_{n-1}$Sb$^+$■, $R_{n-1}$Tl$^+$■, $R_{n-1}$Pb$^+$■, and $R_{n-1}$Bi$^+$■, with n=2 for the In and Tl compounds, n=3 for the Sn and Pb compounds, and n=4 for the Sb and Bi compounds, is stabilized by the group R (e.g., Ph). The stabilization mechanism is visualized exemplary for Sn, Sb, and Bi in FIG. 3.

When the reaction (i.e., radical cleavage and stabilization) is completed, a proton (H$^+$) is released along with a degradation product in which In, Sn, Sb, Tl, Pb, or Bi is in a reduced oxidation state. The oxidation state of In, Sn, Sb, Tl, Pb, and Bi must be reduced by two elementary charges (see FIG. 3, Sn: 4+ to 2+; Sb and Bi: 5+ to 3+).

Due to their delocalized electrons, aryl groups or aromatic cycles or unsaturated heterocyclic groups are more stable and thus particularly suitable as R groups, compared, for example, to alkyl groups. Preferred R groups include aromatic cycles such as phenyl, naphthyl or their derivatives or unsaturated heterocycles such as pyrimidyl, thiophenyl or their derivatives.

The released proton (H$^+$) combines with the photoacid generator's anion, as described in detail below, to form the Brønsted acid (or, in some cases, a Lewis acid), that further participates in the photolithography process.

Surprisingly, the present invention provides a photoacid generator compound cation and a photoacid generator, comprising said photoacid generator compound cation, that have a high absorption cross section for photons in the EUV to increase the sensitivity of chemical amplified photoresists for EUV lithography.

Figure 3:
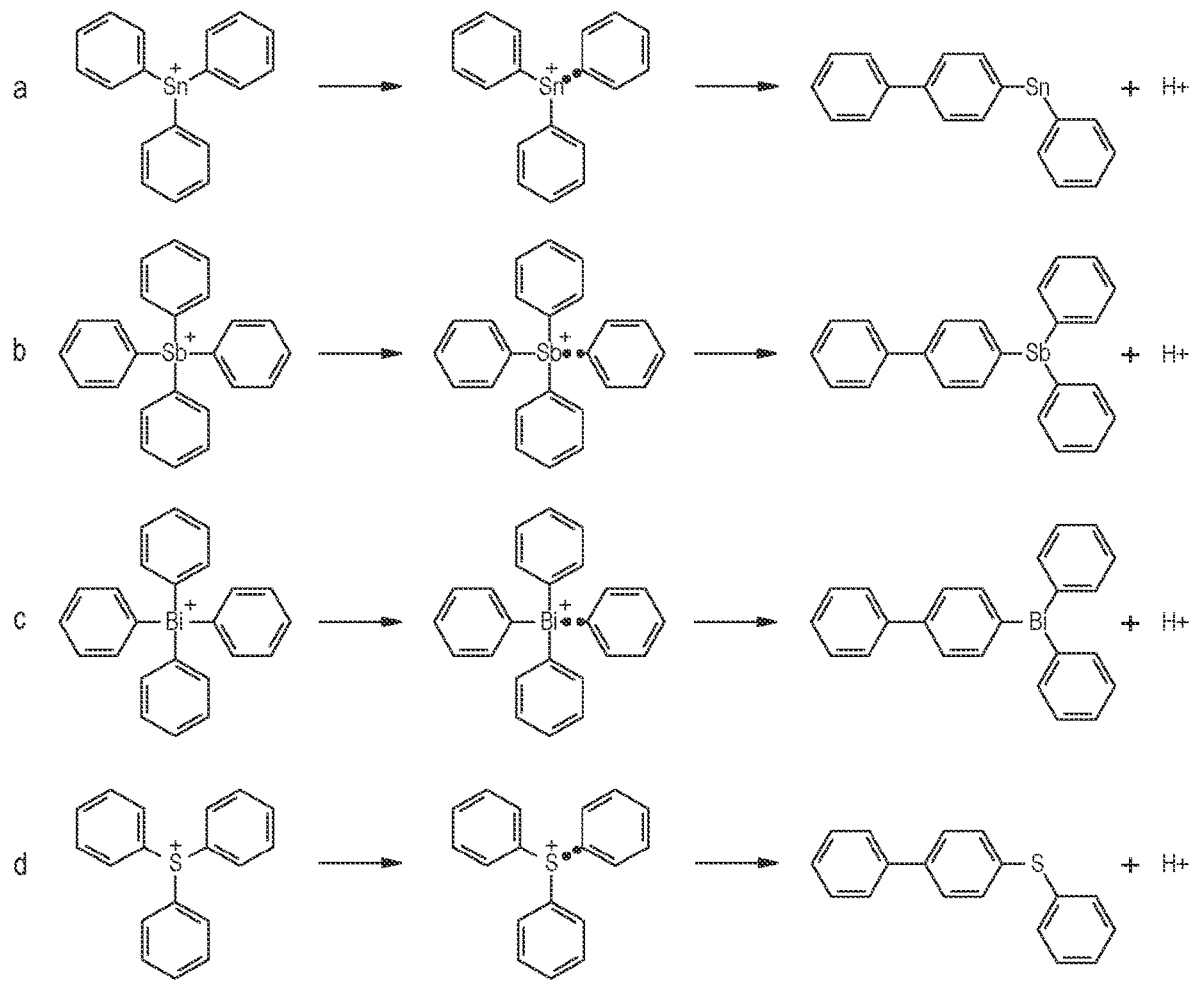
FIG. 3 shows
(a) PAG cation triphenyltin ($Ph_3Sn^+$, with Sn(IV)), Sn—C radical bond cleavage and intermediate radicals (Ph■ and $Ph_2Sn^+$■), and proton $H^+$ release and degradation product with Sn(II) according to the present invention;
(b) PAG cation tetraphenylantimony ($Ph_4Sb^+$, with Sb(V)), Sn—C radical bond cleavage and intermediate radicals (Ph■ and $Ph_3Sb^+$■), and proton $H^+$ release and degradation product with Sb(III) according to the present invention;
(c) PAG cation tetraphenylbismuth ($Ph_4Bi^+$, with Bi(V)), Bi—C radical bond cleavage and intermediate radicals (Ph■ and $Ph_3Bi^+$■), and proton $H^+$ release and degradation product with Bi(III) according to the present invention; and
(d) for reference only: PAG cation triphenylsulfonium ($Ph_3S^+$, with Sn(IV)), S—C radical bond cleavage and intermediate radicals (Ph■ and $Ph_2S^+$■), and proton $H^+$ release and degradation product with S(II), in accordance with an embodiment of the present invention.

Ab initio simulations, which are computational chemistry methods based on quantum chemistry, of the photoreactions shown in FIG. 3, in gas phase, at 0 K, and at the Perdew-Burke-Esnzerof and double-zeta valence polarisations (PBE/DZP) level of theory, were performed. For the first step of the photodissociation for the Sn, Sb, and Bi compounds, reaction energies of 76, 70, and 60 kcal/mol, respectively, were obtained. For reference or contextual purposes only, for the prior art S compound, the reaction energy is 71 kcal/mol (Journal of Photopolymer Science and Technology, 9, 587 (1996)). Hence, the Sn, Sb, and Bi compounds have a dissociation energy which is similar to the dissociation energy of the prior art S compound. Hence, the Sn, Sb, and Bi compounds can be used in the photoreactions shown in FIG. 3.

Figure 4:
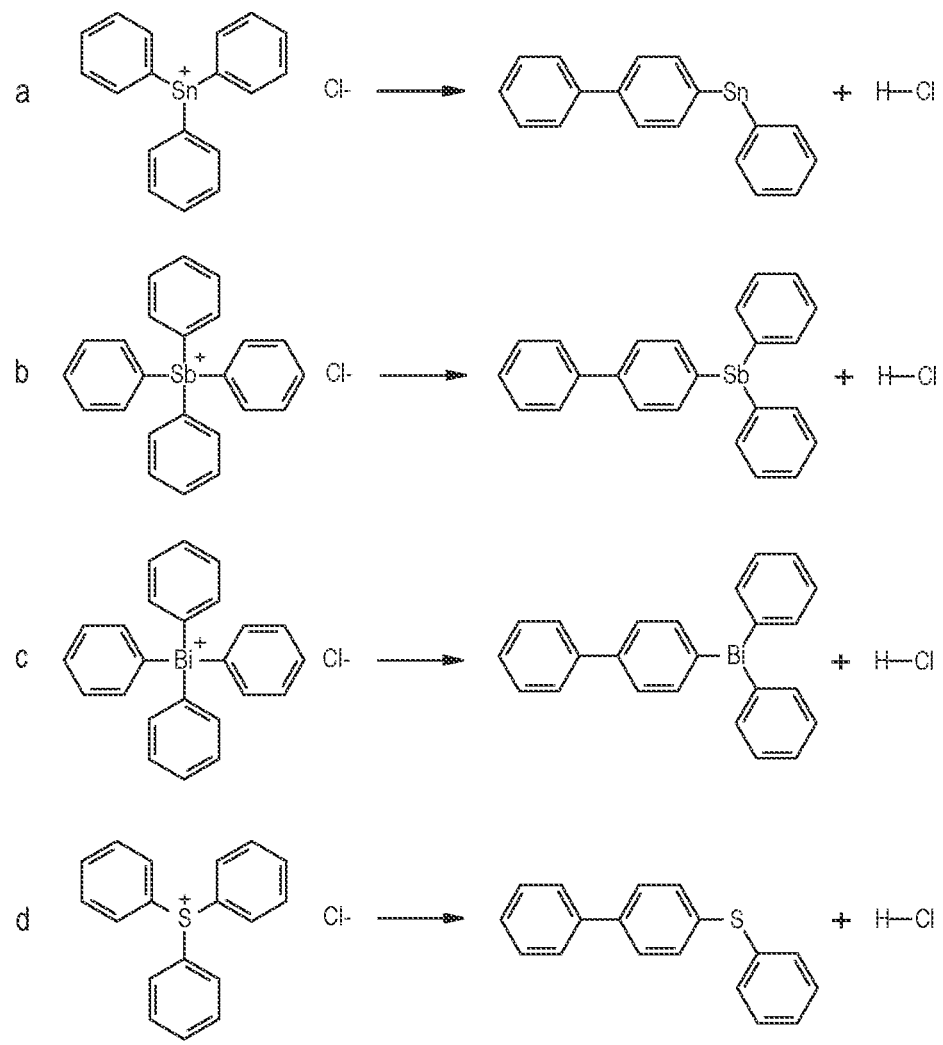
FIG. 4 displays
(a) PAG triphenyltin chloride decomposition and HCl acid generation;
(b) PAG tetraphenylantimony chloride decomposition and HCl acid generation;
(c) PAG tetraphenylbismuth chloride decomposition and HCl acid generation; and
(d) for reference only: PAG triphenylsulfonium chloride decomposition and HCl acid generation, in accordance with an embodiment of the present invention.

Additionally, ab initio simulations of the photoreactions shown in FIG. 4, in gas phase, at 0 K, and at the PBE/DZVP level of theory, were performed. For the photoreactions for the Sn, Sb, and Bi compound, reaction energies of +29, −18, and −33 kcal/mol, respectively, were obtained. For reference or contextual purposes only, for the prior art S compound, the reaction energy is −36 kcal/mol. Thus, the Sb and Bi compounds have favorable reaction energies. The reaction energy of the Bi compound is similar to the reaction energy of the prior art S compound. The Sn compound has a positive reaction energy due to the relative instability of the Sn(II) compound compared to the Sn(IV) compound. Hence, the Sb and Bi compounds, and very likely the Sn compound, can be used in the photoreactions shown in FIG. 4.

Figure 5:
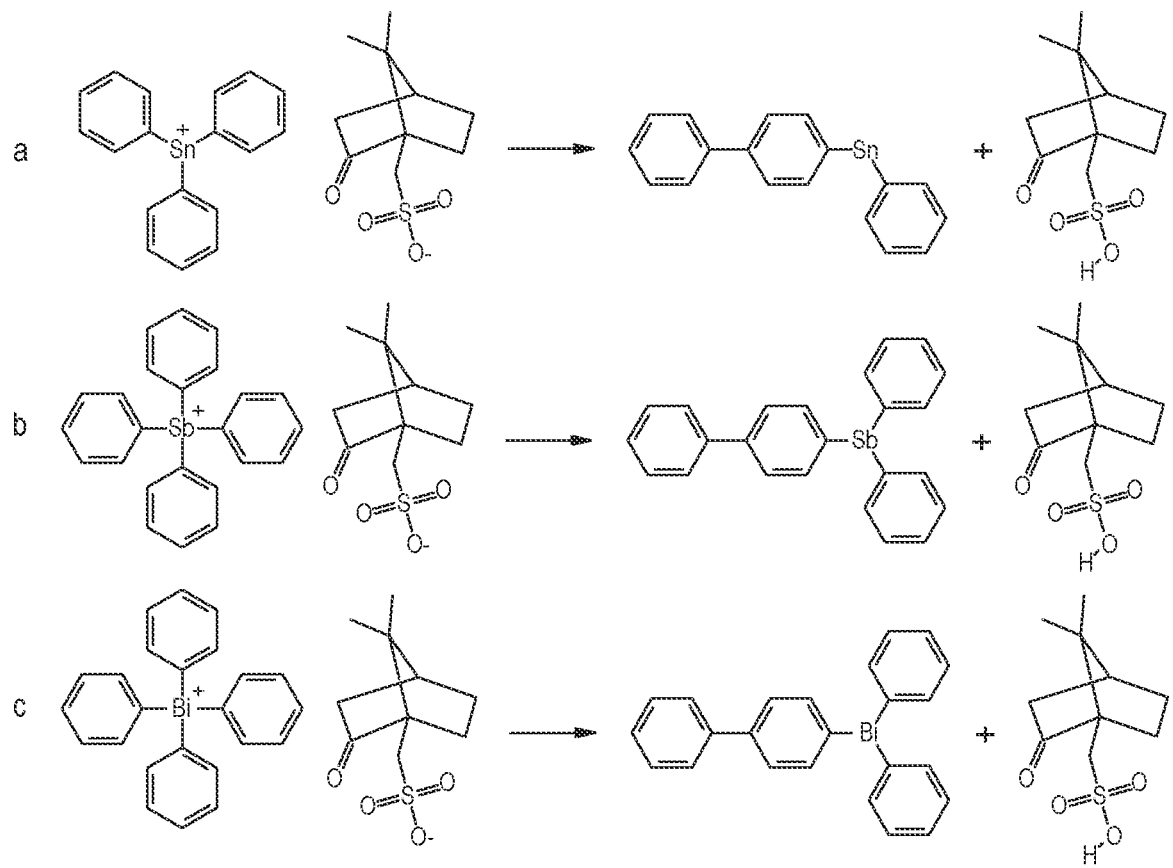
FIG. 5 displays
(a) PAG triphenyltin camphorsulfonate decomposition and camphorsulfonic acid generation;
(b) PAG tetraphenylantimony camphorsulfonate decomposition and camphorsulfonic acid generation; and (c) PAG tetraphenylbismuth camphorsulfonate decomposition and camphorsulfonic acid generation, in accordance with an embodiment of the present invention.

Persons with an ordinary skill in the art will realize that ab initio simulations of photoreactions of the Sn, Sb, and Bi compounds with other anions, for example, ab initio simulations of photoreactions shown in FIG. 5, would yield similar respective reaction energies.

The above described ab initio simulations demonstrate that the preferred embodiments of the photoacid generator compound cation, namely tetraphenylantimony, tetraphenylbismuth, and very likely triphenyltin, can be used advantageously in photoreaction. Hence, due to said advantageous properties, the most preferred elements X in the photoacid generator compound cation according to the present invention are antimony, bismuth, and tin, and the most preferred groups R in the photoacid generator compound cation according to the present invention is phenyl.

However, persons with an ordinary skill in the art will realize that in the photoreactions described in detail above also other, i.e., modified, photoacid generator compound cations according to the present invention with alternatives groups R, such as naphthyl or saturated or unsaturated heterocyclic group, etc., as defined above, or with at least two R groups that are linked with each other via a covalent bond or a linking atom or linking group between any of two carbon atoms of two R groups as defined above, can be used.

In a most preferred variant, two of the R groups of the element X in the photoacid generator cation are linked with each other, which influences the rotational degrees of freedom or resonance behavior of the photoacid generator compound cation, via a covalent bond between any of two C atoms of the two R groups. Hence, due to said advantageous properties, the most preferred photoacid generator compound cations according to the present invention are 2,2'-biphenylylene-diphenylantimony, 2,2'-biphenylylene-diphenylbismuth, and 2,2'-biphenylylene-phenyltin.

The photoacid generator compound according to the present invention further comprises an anion. The anion is a conventional or typical anion used for photoacid generators, and there are numerous derivatives taught in the art.

Preferably, the photoacid generator according to the present invention includes a combination of the photoacid generator compound cation according to the present invention with known-fluorine-free anions such as camphorsulfonate and p-toluenesulfonate, or known fluorinated anions such as trifluoromethanesulfonate, perfluoro-1-butanesulfonate, hexafluorophosphate, hexafluoroantimonate, tetrakis(pentafluorophenyl)borate, tris(trifluoromethanesulfonyl)methide, hexafluoropropane-1,3-disulfonimide, bis(trifluoromethenesulfonyl)amide, perfluorobutane-1,4-disulfonate, 2-(trifluoromethyl)benzenesulfonate and derivatives thereof.

Figure 6:
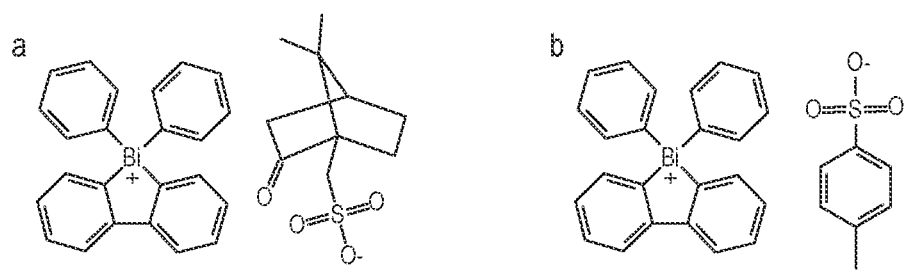
FIG. 6 shows preferred fluorine-free PAGs, in accordance with an embodiment of the present invention:
(a) 2,2'-biphenylylene-diphenylbismuth camphorsulfonate; and
(b) 2,2'-biphenylylene-diphenylbismuth p-toluenesulfonate, in accordance with an embodiment of the present invention.

FIG. 6 depicts preferred embodiments of the photoacid generators on the basis of the photoacid generator compound cation 2,2'-biphenylylene-diphenylbismuth in combination with fluorine-free anions:
  (a) 2,2'-biphenylylene-diphenylbismuth camphorsulfonate; and
  (b) 2,2'-biphenylylene-diphenylbismuth p-toluenesulfonate.

Figure 7:
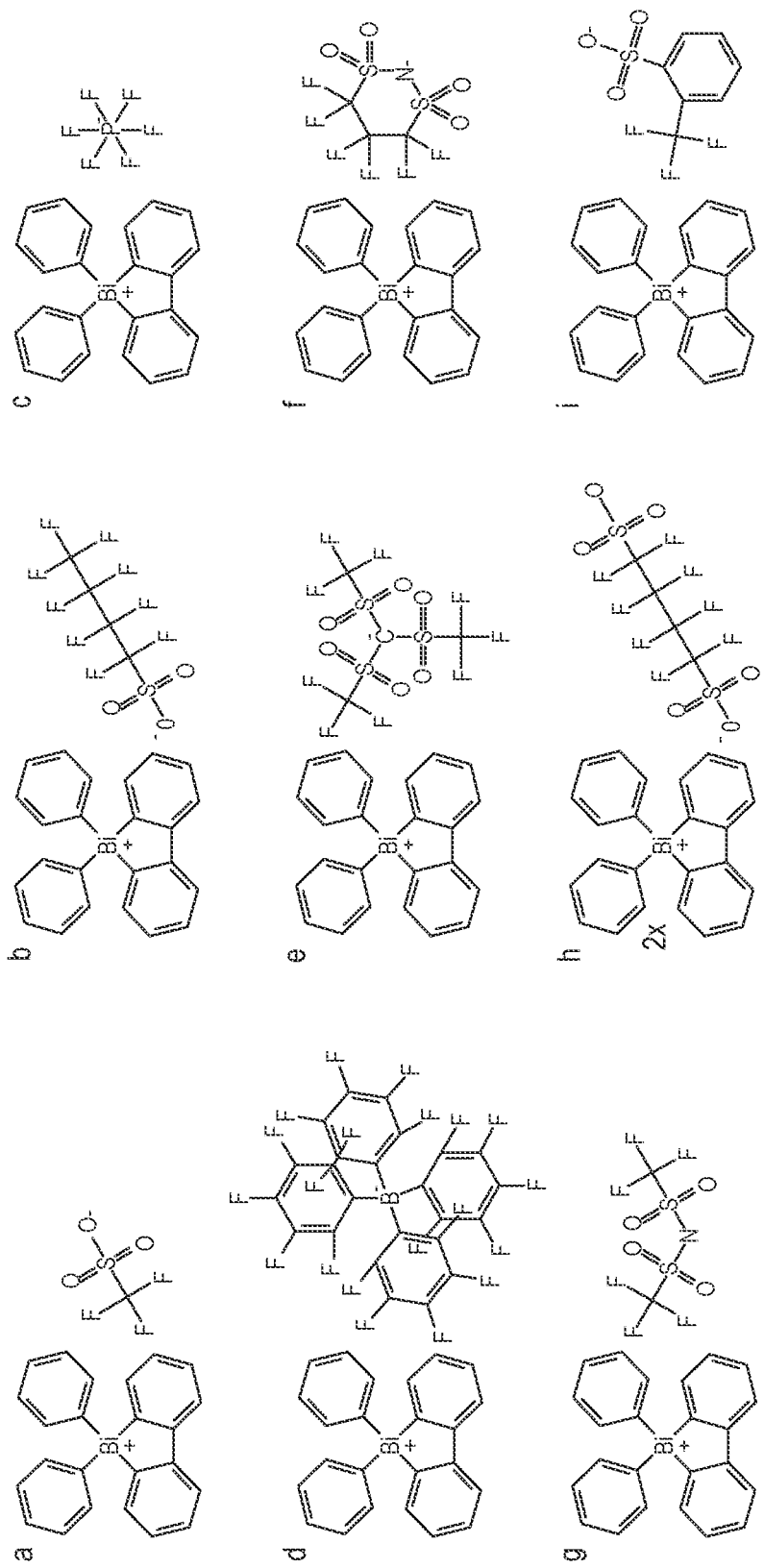
FIG. 7 displays preferred fluorinated PAGs according to the present invention:
(a) 2,2'-biphenylylene-diphenylbismuth trifluormethanesulfonate;
(b) 2,2'-biphenylylene-diphenylbismuth perfluoro-1-butanesulfonate;
(c) 2,2'-biphenylylene-diphenylbismuth hexafluorophosphate;
(d) 2,2'-biphenylylene-diphenylbismuth tetrakis(pentafluorophenyl)borate;
(e) 2,2'-biphenylylene-diphenylbismuth tris(trifluoromethanesulfonyl)methide;
(f) 2,2'-biphenylylene-diphenylbismuth hexafluoropropane-1,3-disulfonimide;
(g) 2,2'-biphenylylene-diphenylbismuth bis(trifluoromethanesulfonyl)amide;
(h) bis(2,2'-biphenylylene-diphenylbismuth) perfluorobutane-1,4-disulfonate; and
(i) 2,2'-biphenylylene-diphenylbismuth 2-(trifluoromethyl)benzenesulfonate, in accordance with an embodiment of the present invention.

FIG. 7 depicts preferred embodiments of the photoacid generators on the basis of the photoacid generator compound cation 2,2'-biphenylylene-diphenylbismuth in combination with fluorinated anions
  (a) 2,2'-biphenylylene-diphenylbismuth trifluormethanesulfonate;
  (b) 2,2'-biphenylylene-diphenylbismuth perfluoro-1-butanesulfonate;
  (c) 2,2'-biphenylylene-diphenylbismuth hexafluorophosphate;
  (d) 2,2'-biphenylylene-diphenylbismuth tetrakis(pentafluorophenyl)borate;
  (e) 2,2'-biphenylylene-diphenylbismuth tris(trifluoromethanesulfonyl)methide;
  (f) 2,2'-biphenylylene-diphenylbismuth hexafluoropropane-1,3-disulfonimide;
  (g) 2,2'-biphenylylene-diphenylbismuth bis(trifluoromethanesulfonyl)amide;
  (h) bis(2,2'-biphenylylene-diphenylbismuth) perfluorobutane-1,4-disulfonate; and
  (i) 2,2'-biphenylylene-diphenylbismuth 2-(trifluoromethyl)benzenesulfonate.

In a more preferred variant, the photoacid generator according to the present invention is selected from the group consisting of:
triphenyltin camphorsulfonate,
triphenyltin p-toluenesulfonate,
triphenyltin trifluoromethenesulfonate,
triphenyltin perfluoro-1-butanesulfonate,
triphenyltin hexafluorophosphate,
triphenyltin hexafluoroantimonate,
triphenyltin tetrakis(pentafluorphenyl)borate,
triphenyltin tris(trifluoromethanesulfonyl)methide,
triphenyltin hexafluoropropane-1,3-disulfonimide,
triphenyltin bis(trifluoromethenesulfonyl)amide,
bis(triphenyltin) perfluorbutane-1,4-disulfonate,
triphenyltin 2-(trifluormethyl)benzenesulfonate,
2,2'-biphenylylene-phenyltin camphorsulfonate,
2,2'-biphenylylene-phenyltin p-toluenesulfonate,
2,2'-biphenylylene-phenyltin trifluoromethenesulfonate,
2,2'-biphenylylene-phenyltin perfluoro-1-butanesulfonate,
2,2'-biphenylylene-phenyltin hexafluorophosphate,
2,2'-biphenylylene-phenyltin hexafluoroantimonate, 2,2'-biphenylylene-phenyltin tetrakis(pentafluorphenyl)borate,
2,2'-biphenylylene-phenyltin tris(trifluoromethanesulfonyl)methide,
2,2'-biphenylylene-phenyltin hexafluoropropane-1,3-disulfonimide,
2,2'-biphenylylene-phenyltin bis(trifluoromethenesulfonyl)amide,
bis(2,2'-biphenylylene-phenyltin) perfluorbutane-1,4-disulfonate,
2,2'-biphenylylene-phenyltin 2-(trifluormethyl)benzenesulfonate,
tetraphenylantimony camphorsulfonate,
tetraphenylantimony p-toluenesulfonate,
tetraphenylantimony trifluoromethenesulfonate,
tetraphenylantimony perfluoro-1-butanesulfonate,
tetraphenylantimony hexafluorophosphate,
tetraphenylantimony hexafluoroantimonate,
tetraphenylantimony tetrakis(pentafluorphenyl)borate,
tetraphenylantimony tris(trifluoromethanesulfonyl)methide,
tetraphenylantimony hexafluoropropane-1,3-disulfonimide,
tetraphenylantimony bis(trifluoromethenesulfonyl)amide,
bis(tetraphenylantimony) perfluorbutane-1,4-disulfonate,
tetraphenylantimony 2-(trifluormethyl)benzenesulfonate,
2,2'-biphenylylene-diphenylantimony camphorsulfonate,
2,2'-biphenylylene-diphenylantimony p-toluenesulfonate,
2,2'-biphenylylene-diphenylantimony trifluoromethenesulfonate,
2,2'-biphenylylene-diphenylantimony perfluoro-1-butanesulfonate,
2,2'-biphenylylene-diphenylantimony hexafluorophosphate,
2,2'-biphenylylene-diphenylantimony hexafluoroantimonate,
2,2'-biphenylylene-diphenylantimony tetrakis(pentafluorphenyl)borate,
2,2'-biphenylylene-diphenylantimony tris(trifluoromethanesulfonyl)methide,
2,2'-biphenylylene-diphenylantimony hexafluoropropane-1,3-disulfonimide,
2,2'-biphenylylene-diphenylantimony bis(trifluoromethenesulfonyl)amide,
bis(2,2'-biphenylylene-diphenylantimony) perfluorbutane-1,4-disulfonate,
2,2'-biphenylylene-diphenylantimony 2-(trifluormethyl)benzenesulfonate,
tetraphenylbismuth camphorsulfonate,
tetraphenylbismuth p-toluenesulfonate,
tetraphenylbismuth trifluoromethenesulfonate,
tetraphenylbismuth perfluoro-1-butanesulfonate,
tetraphenylbismuth hexafluorophosphate,
tetraphenylbismuth hexafluoroantimonate,
tetraphenybismuth tetrakis(pentafluorphenyl)borate,
tetraphenylbismuth tris(trifluoromethanesulfonyl)methide,
tetraphenylbismuth hexafluoropropane-1,3-disulfonimide,
tetraphenylbismuth bis(trifluoromethenesulfonyl)amide,
bis(tetraphenylbismuth) perfluorbutane-1,4-disulfonate,
tetraphenylbismuth 2-(trifluormethyl)benzenesulfonate,
2,2'-biphenylylene-diphenylbismuth camphorsulfonate,
2,2'-biphenylylene-diphenylbismuth p-toluenesulfonate,
2,2'-biphenylylene-diphenylbismuth trifluoromethenesulfonate,
2,2'-biphenylylene-diphenylbismuth perfluoro-1-butanesulfonate,
2,2'-biphenylylene-diphenylbismuth hexafluorophosphate,
2,2'-biphenylylene-diphenylbismuth hexafluoroantimonate,
2,2'-biphenylylene-diphenylbismuth tetrakis(pentafluorphenyl)borate,
2,2'-biphenylylene-diphenylbismuth tris(trifluoromethanesulfonyl)methide,
2,2'-biphenylylene-diphenylbismuth hexafluoropropane-1,3-disulfonimide,
2,2'-biphenylylene-diphenylbismuth bis(trifluoromethenesulfonyl)amide,
bis(2,2'-biphenylylene-diphenylbismuth) perfluorbutane-1,4-disulfonate, and
2,2'-biphenylylene-diphenylbismuth 2-(trifluormethyl)benzenesulfonate.

In a particular preferred variant, the photoacid generator according to the present invention includes 2,2'-biphenylylene-diphenylbismuth camphorsulfonate or 2,2'-biphenylylene-diphenylbismuth p-toluenesulfonate.

However, persons with an ordinary skill in the art will realize that in the photoreactions described in detail above also other, i.e., modified, photoacid generator compound anions, e.g., substituted anions, complex anions, etc., can be used.

The synthesis of the PAG according to the present invention is described exemplary for the PAG tetraphenylbismuth p-toluenesulfonate: First triphenylbismuth is derived from BiCl$_3$ by substitution with three equivalents of a phenyl lithium reagent in a tetrahydrofuran solvent at a temperature of −78° C. Thereafter triphenylbismuth is treated with thionyl chloride as an oxidizing agent in dichloromethane solvent at −78° C. to yield triphenylbismuth dichloride. Then tetraphenylbismuth chloride is produced from triphenylbismuth dichloride by displacement of a Bi—Cl bond with a phenyl lithium reagent in tetrahydrofuran solvent at −78° C. Finally, tetraphenylbismuth p-toluenesulfonate is obtained by treating tetraphenylbismuth chloride with a solution of silver p-toluenesulfonate. People with an ordinary skill in the art will realize that other photoacid generators according to the present invention can be synthesized along the same lines.

Due to their distinguished properties as described above, the photoacid generator, comprising the photoacid generator compound cation according to the present invention, can be formulated into polymer compositions that are useful in lithographic processes, especially when EUV irradiation is used.

Hence, in a further aspect, the present invention relates to a photoresist composition, comprising:
(a) a photoacid generator compound according to the present invention; and
(b) an acid labile polymer.

The acid labile polymer is preferably capable of undergoing chemical transformations upon exposure of the photoresist composition, in particular DUV irradiation or EUV irradiation, whereby a differential in the solubility of the polymer in either the exposed regions or the unexposed regions is created. In such a polymer, the acid sensitivity exists because of the presence of acid sensitive side chains that are bonded to the polymer backbone. Such acid sensitive polymers including acid sensitive side chains are conventionally.

The acid labile imaging polymer used according to the present invention preferably is selected from a copolymer such as poly(p-hydroxy styrene)-r-poly(t-butyl acrylate) and a terpolymer such as poly(p-hydroxy styrene)-r-poly(styrene)-r-poly(t-butyl acrylate).

The content of the photoacid generator compound according to the present invention in the photoresist composition is preferably 1 to 30% by weight, and more preferably 5 to 20% by weight, based on the total weight of the photoresist composition.

The photoresist compositions of the invention preferably contain a solvent which is capable of dissolving the acid sensitive imaging polymer and the photoacid generator. Examples of such solvents include, but are not limited to, ethers, glycol ethers, aromatic hydrocarbons, ketones, esters and the like. A solvent system including a mixture of the aforementioned solvents is also contemplated herein. Suitable glycol ethers include 2-methoxyethyl ether (diglyme), ethylene glycol monomethyl ether, propylene glycol monomethyl ether, propylene glycol monomethylether acetate (PGMEA) and the like. Suitable aromatic hydrocarbon solvents include toluene, xylene, and benzene. Examples of ketones include methylisobutylketone, 2-heptanone, cycloheptanone, and cyclohexanone. An example of an ether solvent is tetrahydrofuran, whereas ethyl lactate and ethoxy ethyl propionate are examples of ester solvents that may be employed herein.

In addition to the above components, the photoresist composition may also include other components such as a base quencher, a photosensitizer, a pigment, a filler, an antistatic agent, a flame retardant, a defoaming agent, a light stabilizer, an antioxidant, or other additives. If desired, combinations or mixtures of these other components may be used.

Chemically amplified photoresists for EUV lithography that comprise the photoacid generator compound cation and the photoacid generator according to the present invention have a high absorption cross section for photons in the EUV, and thus, have an increased sensitivity in the EUV.

Preferably, chemically amplified photoresists for EUV lithography that comprise the organobismuth photoacid generator described herein, which have a high absorption cross section for photons in the EUV, are particularly appealing as they are the least toxic compounds among the heavy metals (Jingfei Luan, Lingyan Zhang and Zhitian Hu, Molecules, 16, 4194 (2011)). Additionally, bismuth compounds have a cost advantage. Preferably, the embodiments of the fluorine-free photoacid generators such as 2,2'-biphenylylene-diphenylbismuth camphorsulfonate and 2,2'-biphenylylene-diphenylbismuth p-toluenesulfonate have a material's toxicity and chemical waste advantage over, for example, organotin or organoantimony compounds (taught in here, and in, for example, U.S. Pat. No. 10,642,153 for said inorganic photoresists), and fluorinated photoacid generators.

Chemically amplified photoresists for EUV lithography that comprise the photoacid generator compound cation and the photoacid generator described herein, also pose limited process-integration risks because the process flow in the fab's photobay is unchanged.

In a further aspect, the present invention also encompasses a method of using the photoresist composition of the invention for generating an acid. Said method comprises the steps: applying a photoresist composition (i.e., an embodiment of the present invention), containing the photoacid generator according to the invention, to a substrate; and irradiating patternwise the photoresist composition with an energy ray to cause the photoacid generator to generate an acid.

As substrate in the present invention is suitable any substrate conventionally used in processes involving photoresists. For example, the substrate can be silicon, silicon oxide, aluminium, aluminium oxide, gallium arsenide, ceramic, quartz, copper or any combination thereof, including multilayers.

In a preferred variant of the method according to the present invention, the energy ray with which the patternwise irradiation of the photoresist composition is conducted, is a DUV irradiation or preferably an EUV irradiation.

In a further aspect, the present invention also encompasses a method for using the photoresist composition of the invention to form patterned material features on a substrate comprising a material surface which may comprise a metal conductor layer, a ceramic insulator layer, a semiconductor layer or other material depending on the stage of the manufacture process and the desired material set for the end product. The photoresist composition of the invention is especially useful for EUV lithographic processes used in the manufacture of integrated circuits on semiconductor substrates. The photoresist composition of the invention used in lithographic processes create patterned material layer structures such as metal wiring lines, holes for contacts or vias, insulation sections (e.g., damascene trenches or shallow trench isolation), trenches for capacitor structures, ion implanted semiconductor structures for transistors, and the like as might be used in integrated circuit devices.

After exposure, the photoresist structure with the desired pattern is obtained or developed by contacting the photoresist layer with an aqueous alkaline solution which selectively dissolves the areas of the photoresist which were exposed to radiation in the case of a positive photoresist (or the unexposed areas in the case of a negative photoresist). Some aqueous alkaline solutions or developers comprise aqueous solutions of tetramethyl ammonium hydroxide. The resulting lithographic structure on the substrate is then typically dried to remove any remaining developer. If a top coat has been used, it can be dissolved by the developer in this step.

The pattern from the photoresist structure may then be transferred to the exposed portions of underlying material of the substrate by etching with a suitable etchant using techniques known in the art. In one embodiment the transfer is done by reactive ion etching or by wet etching. Once the desired pattern transfer has taken place, any remaining photoresist may be removed using conventional stripping techniques. Alternatively, the pattern may be transferred by ion implantation to form a pattern of ion implanted material.

In a preferred variant of the method according to the present invention, the energy ray with which the patternwise irradiation of the photoresist composition is conducted, is a DUV irradiation or preferably an EUV irradiation.

What is claimed is:

1. A computer-implemented method comprising:
generating an acid, wherein generating an acid comprises:
applying a photoresist composition to a substrate, wherein the photoresist has increased sensitivity to EUV light by adding a photoacid generator having an element X, wherein X has a large absorption cross section at 92 eV photos of at least $0.5 \times 10^7$ cm$^2$/mol and has at least two stable oxidation states; and
irradiating the photoresist composition with an energy ray to cause the photoacid generator to generate an acid.

2. The computer-implemented method according to claim 1, wherein the energy ray is a deep ultraviolet (DUV) irradiation or an extreme ultraviolet (EUV) irradiation.

3. The computer-implemented method of claim 1, further comprising:
forming a patterned materials features on a substrate, wherein forming a patterned materials features on a substrate comprises:
providing a material surface on a substrate;
forming a layer of the photoresist composition over said material surface;

patternwise irradiating the photoresist layer with an energy ray thereby creating a pattern of radiation-exposed regions in said photoresist layer;

selectively removing portions of said photoresist layer to form exposed portions of said material surface; and etching or ion implanting said exposed portions of said material, thereby forming said patterned material feature.

4. The computer-implemented method according to claim 2, wherein the energy ray is a deep ultraviolet (DUV) irradiation or an extreme ultraviolet (EUV) irradiation.

* * * * *